United States Patent [19]
Finley

[11] Patent Number: 5,293,648
[45] Date of Patent: Mar. 15, 1994

[54] TAG FOR VISUALLY INDICATING LOSS OF A PROTECTIVE AGENT

[75] Inventor: Randolph L. Finley, Upper Montclair, N.J.

[73] Assignee: Galey & Lord, Incorporated, Greensboro, N.C.

[21] Appl. No.: 783,142

[22] Filed: Oct. 28, 1991

[51] Int. Cl.$^5$ .................. D06P 5/00; G01N 21/00
[52] U.S. Cl. ........................... 2/243.1; 8/490; 116/206; 252/608; 428/920; 428/921; 422/55; 422/119
[58] Field of Search ............... 422/50, 55, 56, 119, 422/116, 8; 116/206; 8/490; 2/79, 115, 243 A, 243 R, 244; 252/608; 428/920, 921

[56] References Cited

U.S. PATENT DOCUMENTS

| | | | |
|---|---|---|---|
| 1,224,145 | 5/1917 | Craig | 8/111 |
| 2,108,838 | 4/1935 | Whitehead | 8/400 |
| 3,030,227 | 4/1962 | Clifford et al. | 428/207 |
| 3,590,772 | 7/1971 | Boone | 73/762 |
| 3,698,016 | 10/1972 | Saddler | 2/243 R |
| 4,311,479 | 1/1982 | Fenn et al. | 8/495 |
| 4,389,448 | 6/1983 | Green | 428/195 |
| 4,392,315 | 7/1983 | Irving et al. | 8/925 X |
| 4,588,409 | 5/1986 | Sercus | 8/403 |
| 4,902,300 | 2/1990 | Johnson et al. | 8/584 X |
| 4,909,179 | 3/1990 | McBride | 116/206 |
| 5,064,440 | 11/1991 | Howard et al. | 8/543 X |

FOREIGN PATENT DOCUMENTS 48-17622 5/1973 Japan.
62-179640 8/1987 Japan.

Primary Examiner—James C. Housel
Assistant Examiner—Maureen M. Wallenhorst
Attorney, Agent, or Firm—Bell, Seltzer, Park & Gibson

[57] ABSTRACT

An indicator tag is provided for visually indicating the remaining effectiveness of a protective chemical treatment agent on a textile article. The tag is made from a fabric dyed with at least one dye to impart to the piece of fabric a predetermined initial color which indicates that the chemical treatment agent on the textile article is effective. The dye has a chromophore which is susceptible to degradation by reagents which would destroy the effectiveness of the chemical treatment agent so that exposure of the indicator tag to such reagents causes the indicator tag to change from its predetermined initial color to another color, thereby indicating that the textile article with which the indicator tag is used has been exposed to reagents which may cause a loss in the effectiveness of the protective chemical treatment agent on the textile article.

27 Claims, 1 Drawing Sheet

TAG FOR VISUALLY INDICATING LOSS OF A PROTECTIVE AGENT

BACKGROUND OF THE INVENTION

This invention relates to an indicator tag for visually indicating the remaining effectiveness of a protective chemical treatment agent on a textile article.

A variety of protective chemical treatments are used to impart a particular desired characteristic to a textile article. Various treatments include flame retardants, antimicrobial agents, antistatic agents and the like. Of particular importance is the application of flame retardants to textile articles. Flame retardants are widely used on textile articles, particularly for fabrics used in various types of wearing apparel, such as children's wearing apparel.

Despite the advantages afforded by the these various protective chemical treatments, the treatments lose their effectiveness under certain conditions. For example, a protective chemical treatment on a textile article may lose its effectiveness gradually by washing away as the article is laundered numerous times. A protective chemical treatment may also lose its effectiveness quickly due to improper handling and laundering of the textile article. For example, exposure of a textile article to an oxidizing agent such as chlorine bleach, may cause immediate loss of the effectiveness of many protective chemical treatment agents.

Many of these protective chemical treatments are not visible to the consumer when applied to a textile article. Because the consumer cannot see the protective treatment on the textile article, he cannot determine when the protective chemical treatment has lost its effectiveness. Therefore, there is a need for indicating a loss of the effectiveness of these protective chemical treatment agents.

U.S. Pat. No. 4,311,479 to Fenn discloses the use of a dye which bonds preferentially to an antimicrobial treatment such that when the dye disappears from the fabric due to washing, there is an indication that the antimicrobial treatment is exhausted. In Fenn, however, the dye is applied as thin stripes or dots or some similar configuration over the entire surface of a substrate impregnated with an antimicrobial agent. Since this affects the overall appearance of the substrate, this restricts significantly the applicability of this treatment.

It would, therefore, be highly desirable to have a simple method of visually indicating the effectiveness of a protective chemical treatment agent without affecting the overall appearance of the substrate thus treated.

SUMMARY OF THE INVENTION

The present invention provides a textile article of manufacture for determining easily and reliably the effectiveness of a protective chemical treatment agent on the textile article. A textile article of manufacture according to the invention comprises, in combination, a textile article which has been treated with a protective chemical treatment agent, such as a flame retardant or antimicrobial agent and an indicator tag attached to the textile article. The indicator tag visually indicates the remaining effectiveness of the protective chemical treatment agent on the textile article.

The indicator tag comprises a piece of fabric of a size significantly smaller than the overall size of the textile article. The fabric incorporates at least one dye which imparts to the piece of fabric a predetermined initial color and indicates that the chemical treatment agent on the textile article is effective. Advantageously, the fabric is treated with the same protective chemical treatment agent used on the textile article so that the particular characteristic achieved for the textile article is not affected by the addition of the indicator tag.

The dye incorporated into the fabric has a chromophore which is susceptible to degradation by reagents which destroy the effectiveness of the chemical treatment agent, such as chlorine bleach for example. Exposure of the textile article to such reagents causes the indicator tag to change from the predetermined initial color to another color, thereby indicating to the user that the fabric has been exposed to agents which can produce a loss in the effectiveness of the protective chemical treatment agent on the textile article.

In a particularly preferred embodiment of the invention, the fabric is designed to indicate when a flame retardant treatment has lost its effectiveness. It may incorporate two or more dyes which collectively impart to the piece of fabric the predetermined initial color which indicates that the flame retardant chemical treatment agent on the textile article has not been exposed to agents which would destroy the flame retardant treatment. The two dyes have different chemical properties and fastness characteristics. At least one of the dyes is substantially unreactive and fast to agents which destroy the effectiveness of the protective flame retardant chemical treatment agent. This dye is selected from the group consisting of vat dyes, fiber reactive dyes and sulfur dyes. At least one other of the dyes has a chromophore which is susceptible to degradation by such agents and is selected from the group consisting of certain fiber reactive dyes and sulfur dyes.

In one aspect of this embodiment, the dyes are of different colors, which when applied to the article give it a third color. When the fabric is exposed to an oxidizing agent such as chlorine bleach, the chromophores of at least one dye are destroyed or altered, thereby changing the color of the indicator tag. In another aspect of this embodiment of the invention, the first dye is darker than the second, thereby imparting its color as the initial predetermined color of the indicator tag. After contact with the oxidizing agent, the first dye is rendered colorless, leaving the second color intact.

The indicator tag may be a label with printed indicia explaining the significance of a change in the color of the label. For example, the printed indicia may explain that a color change indicates the fabric has been exposed to chlorine bleach and that the flame retardancy has therefore been lost. The printed indicia of the label may be visible prior to the color change or may be latent, becoming visible only after the label exhibits a color change from its predetermined color.

From the foregoing, it will be evident that the indicator tag of the present invention, when used on a garment which has been treated with a protective chemical treatment, will provide a visually discernible indication that the garment has been exposed to conditions which would result in loss of the effectiveness of the chemical treatment. The consumer is thus able to determine when the garment should be removed from use, even though the chemical treatment itself is not visible.

DESCRIPTION OF THE DRAWINGS

Some of the features and advantages of the invention having been described, others will become apparent from the detailed description which follows, and from the accompanying drawings, in which.

DETAILED DESCRIPTION OF THE INVENTION

Figure 1:
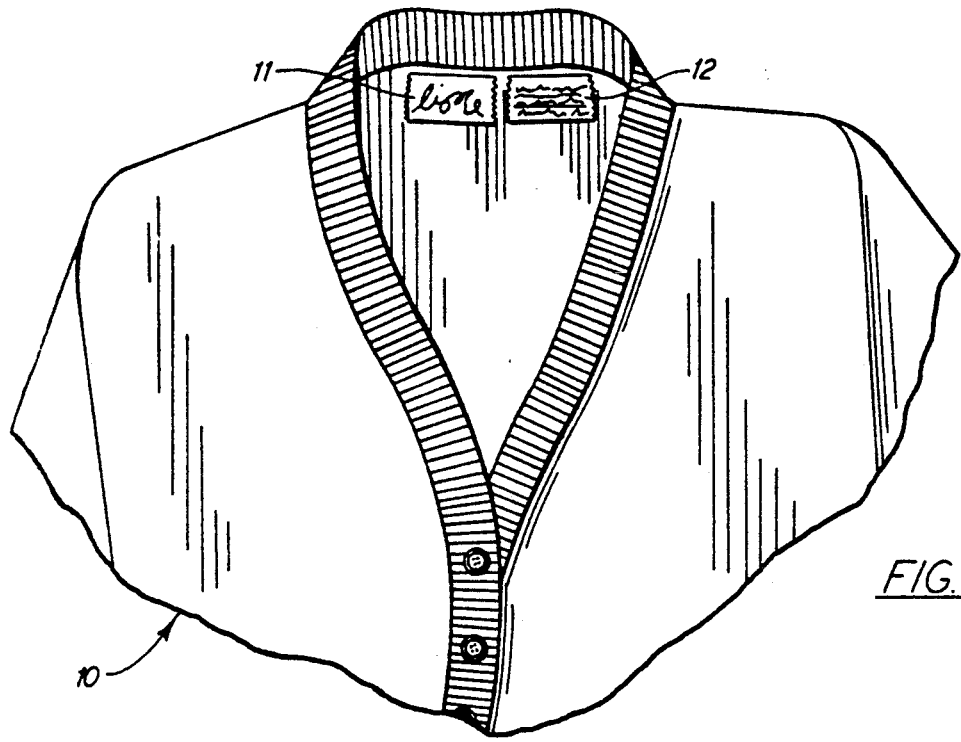
FIG. 1 is a partial front view of a textile garment having an indicator tag.

FIG. 1 illustrates one embodiment of a textile article according to the present invention. The textile article may be any type of garment. The garment illustrated here is a child's pajama top designated broadly as 10. As further illustrated in FIG. 1, the usual type of manufacturer's label 11 is attached to the pajama top 10. An indicator tag 12 in accordance with the present invention is also attached to the pajama top 10.

The garment may be formed of a conventional textile fabric, such as a woven, knitted or nonwoven fabric formed of cellulosic fibers, synthetic fibers, or blends thereof. Further, the fabric of the garment is treated with a protective chemical treatment agent, for example, a flame retardant. Flame retardants are widely used, for example on sleepwear for children and on industrial uniforms and protective garments. There are various types of flame retardants, including phosphorus-based flame retardants. One exemplary phosphorus-based treatment is the application of tetrakishydroxymethyl phosphonium chloride ("THP"). Another example of a phosphorous-based flame retardant is a dialkylphosphonocarboxylic acid amide, such as the flame retardant product sold by Ciba Geigy under the name Pyrovatex CP. Other types of protective chemical treatment agent which may be used include antimicrobial agents, antistatic agents, or various other conventional chemical treatment agents. Such agents are applied to the fabric in any of the ways known in the art.

Most chemical protective treatments of this type are not readily visible to a consumer when applied to a fabric. For example, a fabric treated with a THP-based flame retardant has an appearance not significantly different from an untreated fabric. Because the treatment is not visible to the consumer, there is no way of knowing when its effectiveness is lost and when the garment should be removed from use. Loss of the effectiveness of the protective chemical treatment agent may occur under various conditions. For example, improper laundering conditions, such as exposure to an oxidizing agent, may immediately degrade the protective agent. This is especially true of bleaching agents, and particularly chlorine bleach.

The present invention provides a way for the consumer to determine when the effectiveness of the protective treatment is lost, such as may occur as a result of improper laundering. In accordance with the invention, the indicator tag 12 indicates that the effectiveness of the protective treatment is lost by changing color or by revealing latent indicia.

In FIG. 1, the indicator tag 12 is a label made from a piece of fabric of a size significantly smaller than the overall size of the pajama top 10. The indicator tag 12 may be attached to the treated garment by any of the ways known in the art. For example, in FIG. 1 the indicator tag 12 is sewn to the pajama top 10 along the upper edge of the inner back side of the garment.

The fabric of the indicator tag 12 is dyed to give the piece of fabric a predetermined initial color. The predetermined initial color indicates that the protective chemical treatment of the textile article is effective. In a preferred embodiment of the invention, the fabric is dyed with at least two dyes which collectively impart to the piece of fabric the predetermined initial color. At least two dyes have different chemical properties and fastness characteristics, with at least one of these dyes being substantially unreactive and fast to reagents which would destroy the effectiveness of the chemical treatment agent. This dye may, for example, be either a sulfur or vat dye or fiber reactive dye which exhibits this characteristic. At least another dye has a chromophore which is susceptible to degradation by reagents which would destroy the effectiveness of the chemical treatment. This dye may, for example, be either a fiber reactive or sulfur dye which exhibits this characteristic. Advantageously, the indicator tag fabric is also treated with a protective chemical treatment agent so as to not impair the desired overall characteristic sought for the garment when the indicator tag is attached to the garment.

When the garment is exposed to an oxidizing agent, such as chlorine bleach, which causes the effectiveness of the protective agent on the garment to be lost, the indicator tag changes from its initial predetermined color to another color.

Figure 2:
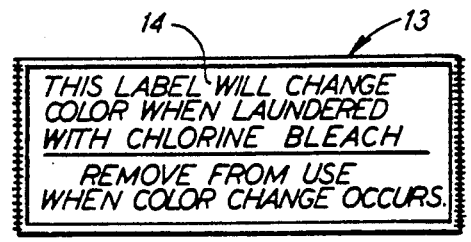
FIG. 2 is a close-up view of the indicator tag of FIG. 1.

The indicator tag of the invention may have printed indicia explaining the significance of a change in the color of the label. FIG. 2 illustrates one embodiment of the indicator tag 13 having such indicia 14. Indicia 14 explain that a color change of the indicator tag indicates that the garment has been laundered with chlorine bleach and that the garment should be removed from use.

Figure 3A:
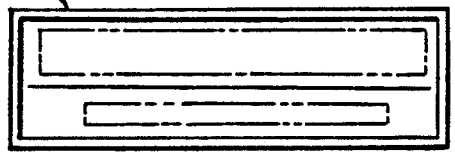
FIGS. 3A and 3B are close-up views of another embodiment of an indicator tag of the invention.
Figure 3B:
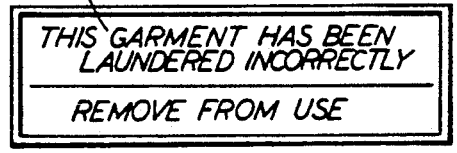

FIGS. 3A and 3B illustrates two views of another aspect of this embodiment of an indicator tag of the invention. In FIG. 3A, an indicator tag 15 includes latent printed indicia analogous to that embodied in FIG. 2. The indicia are printed with at least one dye that is substantially fast and unreactive when exposed to reagents that degrade the protective chemical treatment agent. The printed indicia are covered by at least one other dye with a chromophore which is susceptible to degradation by reagents which would destroy the effectiveness of the chemical treatment. As the garment is exposed to conditions affecting the protective treatment, such as exposure to chlorine bleach, the dye covering the printed indicia disappears or changes color. This exposes the latent indicia as illustrated in FIG. 3B at 16, thereby indicating that the garment has been laundered incorrectly and should be removed from use.

The dyes incorporated in the fabric of the indicator tag include those chosen from vat, sulfur and fiber reactive dyes. Vat dyes are water-insoluble dyes, usually having a carbonyl group, that can be easily reduced, or "vatted," to a water-soluble leuco form. In the vatting process, an alkaline solution, usually sodium hydrosulfite, reduces the carbonyl group to a water-soluble hydroxyl group. The solution, which is often a different color from the original insoluble material, dyes the textile substrate with the shade of vat solution. Upon oxidation with air or other oxidizing agents, the reaction reverses to form the original water-insoluble color, leaving it deposited in the fiber as a pigment.

Two examples of vat dyes are indigos, such as CI# 73000, and anthraquinones, such as Indanthrene Blue BFP, CI# 69285. Vat dyes are outstanding in their fastness to water, light and chemicals.

Sulfur dyes, are also applied by a vatting technique. These dyes are produced by treating a wide variety of organic compounds with sulfur and sodium sulfides. Like vat dyes, sulfur dyes are water-insoluble compounds reduced to a water-soluble form before application and then oxidized to the original water insoluble colored state. The reducing agent may be an alkaline sodium sulfide solution. The dye is applied to the fabric in the soluble form and then oxidized to produce the insoluble dye on the fiber. These colors are mostly used on cotton. Sulfur dyes have moderate all around fastness and are relatively cheap. One example is Sulfur Black, CI# 53185.

Fiber reactive dyes form a covalent bond with a substrate during the dyeing process and are of particular interest on cellulosic fibers. Fiber reactive dyes are water soluble colors that contain a group capable of reacting with the hydroxyl or amino group in cellulose, wool, silk, and other substrates. Two examples of such reactive groups are: (1) active halogen compounds which form ether or amide links; and (2) activated vinyl groups which form ether links. Fiber reactive dyes provide good wash fastness without resorting to the production of large insoluble agglomerates within the fiber such as occurs with vat dyes.

Vat, sulfur, and fiber reactive dyes have varying susceptibilities to oxidizing agents such as bleach. The differences are a result of each's particular chemical structure and its interaction with oxidizing agents. Differences are also a result of the various processes used to apply the dyes to a textile substrate. For example, the chromophores of fiber reactive dyes are subject to degradation by oxidizing agents. In contrast, the chromophores of most vat dyes are unaffected by oxidizing agents such as chlorine bleach. Sulfur dyes, depending upon the particular dyestuff selected, may exhibit either fastness or instability in the presence of a chlorinated oxidizing agent. The fastness of particular dyes to an oxidizing agent, and in particular to chlorine bleach, is known in the art and can be determined by routine tests.

From the foregoing, it is seen that the indicator tag of the invention provides a way for a consumer to determine if a protective chemical treatment on a garment is still effective. When the indicator tag changes color, this indicates to a consumer that the garment has been incorrectly laundered and that the protective treatment is likely to have been compromised. Additionally, the indicator tag may have printed indicia which explain to the consumer the significance of a color change. The consumer can therefore readily and visually assess the effectiveness of the protective treatment on the garment.

The invention can be further understood from the following example.

EXAMPLE 1

A woven fabric was prepared from 100% cotton to give a 6.5 ounce per square yard fabric. Two dyes having different chemical properties and fastness characteristics were selected: Sulfur Red 2B having a good fastness to laundering and chlorine bleach and Sulfur Black 4GCF which is easily degraded by chlorine bleach and washes down during laundering. The dye bath was applied to the fabric in the conventional manner by padding and the fabric was thereafter dried, resulting in a black colored fabric. The thus dyed fabric was printed on the back side with a deca-bromo diphenyl oxide/antimony oxide flame retardant mixture and fixed using an acrylic binding system and heat. The resulting substrate retained its black appearance on the front side.

To test the effectiveness of the fabric as an indicator, a sample of the fabric was laundered by conventional home laundering procedures with a detergent and with chlorine bleach. After laundering, the fabric changed color from black to red, thereby visually indicating that the effectiveness of the flame retardant was impaired.

A second sample of the fabric was subjected to conventional home laundering without bleach. The sample was laundered in 100 cycles and subsequently subjected to vertical flammability testing (FTM-191-5903). The sample exhibited char lengths of less than six inches, indicating that the fabric is flame resistant through about 100 laundering cycles.

EXAMPLE 2

A woven cotton fabric is prepared and dyed as in Example 1, except that it is dyed with a combination of Sulfur Black 1 and Sulfur Red 14. The fabric is initially black, but turns red after laundering with chlorine bleach.

EXAMPLE 3-5

Examples of other combinations of dyestuffs which may be used in producing indicator fabrics in accordance with the present invention are as follows:

3. Reactive Yellow 95
   Vat Blue 66
   Vat Violet 13
4. Vat Red 10
   Sulfur Black 1
5. Vat Yellow 33
   Reactive Blue 19

EXAMPLE 6

A piece of fabric prepared in Example 1 is sized for attachment as a label in a textile garment and is sewn to the inner collar of an infant sleepwear garment pretreated with a flame retardant. The flame retardant is a phosphorus-based flame retardant, tetrakishydroxymethyl phosphonium chloride ("THP"). The sleepwear garment is exposed to chlorine bleach, and the label changes color from black to red.

That which I claim is:

1. A textile article of manufacture comprising in combination:
    a textile article which has been treated with a protective chemical treatment agent, and
    an indicator tag attached to said textile article for visually indicating the remaining effectiveness of said protective chemical treatment agent on said textile article, said tag comprising a piece of fabric of a size significantly smaller than the overall size of said textile article, said fabric incorporating therein at least one dye which imparts to the piece of fabric a predetermined initial color which indicates that the chemical treatment agent on the textile article is effective, said at least one dye having a chromophore which is susceptible to degradation by reagents which would destroy the effectiveness of said chemical treatment agent whereby exposure of the textile article to such reagents causes the indicator tag to change from said predetermined initial color to another color which is indicative of a loss in the effectiveness of said protective chemical treatment agent on the textile article, and wherein said piece of fabric is also treated with said protective chemical treatment agent.

2. The article according to claim 1 wherein said protective chemical treatment agent applied to said textile article and to said piece of fabric comprises a flame retardant composition.

3. The article according to claim 1 wherein said protective chemical treatment agent applied to said textile article and to said piece of fabric comprises a phosphorus-based composition.

4. The article according to claim 1 wherein said protective chemical treatment agent applied to said textile article and to said piece of fabric comprises a antimicrobial composition.

5. An article according to claim 1 wherein said piece of fabric comprises a label attached to the treated textile article by sewing.

6. A textile article of manufacture comprising in combination:

a textile article which has been treated with a protective chemical treatment agent, and an indicator tag attached to said textile article for visually indicating the remaining effectiveness of said protective chemical treatment agent on said textile article, said tag comprising a piece of fabric of a size significantly smaller than the overall size of said textile article, said fabric incorporating therein at least two dyes which collectively impart to the piece of fabric a predetermined initial color which indicates that the chemical treatment agent on the textile article is effective, said at least two dyes being of different chemical properties and fastness characteristics, with at least one of said dyes being substantially unreactive and fast to reagents which would destroy the effectiveness of said chemical treatment agent, and with at least one other of said dyes having a chromophore which is susceptible to degradation by such reagents whereby exposure of the textile article to such reagents causes the indicator tag to change from said predetermined initial color to another color which is indicative of a loss in the effectiveness of said chemical treatment agent on the textile article.

7. The article according to claim 6 wherein the at least one dye which is susceptible to degradation by said reagents is a fiber reactive or sulfur dye which is susceptible to degradation by chlorine bleach.

8. The article according to claim 6 wherein the at least one dye which is substantially fast to said reagents is a sulfur or vat dye which exhibits fastness to chlorine bleach.

9. A textile article of manufacture comprising in combination:

a garment formed of a textile material which has been treated with a flame retardant chemical treatment agent, and an indicator tag attached to said garment for visually indicating the remaining effectiveness of said flame retardant chemical treatment agent on said garment, the flame retardant chemical treatment agent being susceptible to a loss of effectiveness if exposed to chlorine bleach, said tag comprising a piece of fabric of a size significantly smaller than the overall size of said garment, said fabric incorporating therein at least two dyes which collectively impart to the piece of fabric a predetermined initial color which indicates that the flame retardant chemical treatment agent on the garment is effective, said at least two dyes being of different chemical properties and fastness characteristics, with at least one of said dyes being substantially unreactive and fast to chlorine bleach and selected from the group consisting of vat dyes and sulfur dyes, and with at least one other of said dyes having a chromophore which is susceptible to degradation by chlorine bleach and selected from the group consisting of fiber reactive dyes and sulfur dyes, whereby exposure of the garment to chlorine bleach causes the indicator tag to change from said predetermined initial color to another color which is indicative of a loss in the effectiveness of said flame retardant chemical treatment agent on the garment.

10. The article according to claim 9 wherein said piece of fabric is also treated with said flame retardant chemical treatment agent.

11. The article according to claim 9 wherein said flame retardant chemical treatment agent comprises a phosphorus-based composition.

12. The article according to claim 9 wherein said flame retardant chemical treatment agent comprises tetrakishydroxymethyl phosphonium chloride.

13. The article according to claim 9 wherein said flame retardant chemical treatment agent comprises a dialkylphosphonocarboxylic acid amide.

14. The article according to claim 9 wherein said piece of fabric comprises a label attached to the treated garment by sewing.

15. An article according to claim 14 wherein said label includes printed indicia explaining the significance of a change in the color of the label.

16. An article according to claim 9 wherein said piece of fabric comprises a label attached to the treated garment, said label including latent printed indicia which becomes visible only after the label exhibits a color change from said predetermined initial color, said latent printed indicia serving to indicate the need for replacement of the garment due to loss in the effectiveness of said flame retardant chemical treatment agent.

17. An indicator tag for visually indicating the remaining effectiveness of a protective chemical treatment agent on a textile article, such as a flame retardant treated garment, said tag comprising a piece of fabric of a size adapted to be attached to the chemically treated textile article, said fabric incorporating therein at least one dye which imparts to the piece of fabric a predetermined initial color which indicates that the chemical treatment agent on the textile article is effective, said at least one dye having a chromophore which is susceptible to degradation by reagents which would destroy the effectiveness of said chemical treatment agent whereby exposure of the indicator tag to such reagents causes the indicator tag to change from said predetermined initial color to another color which is indicative of a loss in the effectiveness of said protective chemical treatment agent on the textile article, and wherein said piece of fabric is treated with said protective chemical treatment agent.

18. An indicator tag according to claim 17 wherein said protective chemical treatment agent comprises a flame retardant composition.

19. An indicator tag according to claim 18 wherein said flame retardant composition comprises a phosphorus-based composition.

20. An indicator tag according to claim 17 wherein said protective chemical treatment agent comprises a antimicrobial composition.

21. An indicator tag for visually indicating the remaining effectiveness of a protective chemical treatment agent on a textile article, such as a flame retardant treated garment, said tag comprising a piece of fabric of a size adapted to be attached to the chemically treated textile article, said fabric incorporating therein at least two dyes which collectively impart to the piece of fabric a predetermined initial color which indicates that the chemical treatment agent on the textile article is effective, said at least two dyes being of different chemical properties and fastness characteristics, with at least one of said dyes being substantially unreactive and fast to reagents which would destroy the effectiveness of said chemical treatment agent, and with at least one other of said dyes having a chromophore which is susceptible to degradation by such reagents whereby exposure of the indicator tag to such reagents causes the indicator tag to change from said predetermined initial color to another color which is indicative of a loss in the effectiveness of said protective chemical treatment agent on the textile article.

22. An indicator tag according to claim 21 wherein the at least one dye which is susceptible to degradation by said reagents is a fiber reactive or sulfur dye which is susceptible to degradation by chlorine bleach.

23. An indicator tag according to claim 21 wherein the at least one dye which is substantially fast to said reagents is a sulfur or vat dye which exhibits fastness to chlorine bleach.

24. An indicator tag for visually indicating the remaining effectiveness of a flame retardant chemical treatment agent on a textile garment, the flame retardant chemical treatment agent being susceptible to a loss of effectiveness if exposed to chlorine bleach, said tag comprising a piece of fabric of a size adapted to be attached to the flame retardant treated textile garment, said fabric incorporating therein at least two dyes which collectively impart to the piece of fabric a predetermined initial color which indicates that the flame retardant chemical treatment agent on the textile garment is effective, said at least two dyes being of different chemical properties and fastness characteristics, with at least one of said dyes being substantially unreactive and fast to chlorine bleach and selected from the group consisting of vat dyes and sulfur dyes, and with at least one other of said dyes having a chromophore which is susceptible to degradation by chlorine bleach and selected from the group consisting of fiber reactive dyes and sulfur dyes, whereby exposure of the indicator tag to chlorine bleach causes the indicator tag to change from said predetermined initial color to another color which is indicative of a loss in the effectiveness of said flame retardant chemical treatment agent on the textile garment.

25. The indicator tag according to claim 24 wherein said piece of fabric comprises a label adapted to be attached to a flame retardant treated garment by sewing.

26. The indicator tag according to claim 25 wherein said label includes printed indicia explaining the significance of a change in the color of the label.

27. The indicator tag according to claim 24 wherein said piece of fabric comprises a label attached to the treated textile garment, said label including latent printed indicia which becomes visible only after the label exhibits a color change from said predetermined initial color, said latent printed indicia serving to indicate the need for replacement of the garment due to loss in the effectiveness of said flame retardant chemical treatment agent.

* * * * *